United States Patent [19]
Gnau, III et al.

[11] Patent Number: 5,687,839
[45] Date of Patent: *Nov. 18, 1997

[54] CONTAINER FOR DISPOSING OF HAZARDOUS WASTES

[76] Inventors: J. Russell Gnau, III, 2404 Starr, Royal Oak, Mich. 48073; Michael P. Gnau, 2215 Third St., Mandeville, La. 70448; Vincent Americo Valvona, 4405 Cranbrook Trail, Orchard Lake, Mich. 48323; John R. Gnau, Jr., 3894 Peabody Dr., Bloomfield Hills, Mich. 48302

[*] Notice: The term of this patent shall not extend beyond the expiration date of Pat. No. 5,511,657.

[21] Appl. No.: 607,581

[22] Filed: Feb. 27, 1996

Related U.S. Application Data

[63] Continuation of Ser. No. 175,635, Dec. 30, 1993, Pat. No. 5,511,657.

[51] Int. Cl.⁶ .......................... B65D 81/16; B65D 85/42
[52] U.S. Cl. .......................... 206/204; 206/366; 220/910
[58] Field of Search .......................... 206/569, 570, 206/571, 366, 204, 594, 438; 220/908, 910

[56] References Cited

U.S. PATENT DOCUMENTS

| | | | |
|---|---|---|---|
| 3,292,776 | 12/1966 | Penn | 206/366 |
| 3,999,653 | 12/1976 | Haigh et al. | 306/594 |
| 4,127,010 | 11/1978 | Kannankeril | 206/204 |
| 4,466,538 | 8/1984 | Gianni | 206/366 |
| 4,494,652 | 1/1985 | Nelson et al. | 206/366 |
| 4,576,281 | 3/1986 | Kirksey | 206/370 |
| 4,667,821 | 5/1987 | Shillington | 206/366 |
| 4,702,385 | 10/1987 | Shillington et al. | 220/908 |
| 4,715,498 | 12/1987 | Hanifl | 206/366 |
| 4,884,684 | 12/1989 | Bernardin et al. | 206/204 |
| 4,972,950 | 11/1990 | Shillington | 206/366 |
| 4,978,028 | 12/1990 | George et al. | 220/908 |
| 5,024,865 | 6/1991 | Insley | 206/204 |
| 5,031,767 | 7/1991 | Bruno | 220/908 |
| 5,160,021 | 11/1992 | Sibley et al. | 206/204 |
| 5,323,902 | 6/1994 | Palmer et al. | 206/366 |
| 5,511,657 | 4/1996 | Gnau, III et al. | 206/366 X |

Primary Examiner—Jacob K. Ackun
Attorney, Agent, or Firm—Bliss McGlynn, P.C.

[57] ABSTRACT

A container for disposing of hazardous wastes including an inner receptacle adapted to receive and contain the hazardous wastes or etiological agents and an impact resistent outer container with the inner receptacle disposed within the outer container. The container further includes a fluid barrier located between the inner receptacle and the outer container. The fluid barrier acts as an intermediate containment to minimize fluid from passing from the inner receptacle to the outer container in the event the inner receptacle is ruptured.

8 Claims, 3 Drawing Sheets

CONTAINER FOR DISPOSING OF HAZARDOUS WASTES

This is a continuation of U.S. patent application Ser. No. 08/175,635, filed Dec. 30, 1993, now U.S. Pat. No. 5,511,657.

BACKGROUND OF THE INVENTION

1. Technical Field

The subject invention relates to leak and puncture proof receptacles for contaminated medical or otherwise hazardous wastes, or etiological agents and in particular, to such containers which are adapted to receive, store, ship and destroy medical wastes such as used needles, syringes, scalpels, clinical specimens, medical and biological devices or etiological agents.

2. Description Of The Prior Art

One of the major problems facing the medical community today is the safe and proper disposition of used needles, syringes, scalpel blades, etc., commonly referred to as "sharps". In view of the risk of contracting various blood and bodyfluid borne diseases, it is standard procedure for medical personnel today to quickly dispose of sharps shortly after they have been used. In addition, the safe, proper disposal of clinical specimens, and medical or biological devices pose the same type of disease control problems. To that end, many container based disposal systems are known in the prior art and are presently employed in hospitals, clinics and medical laboratories to meet this need. Examples of the state of the art of such containers can be found in U.S. Pat. No. 4,466,538 issued to Gianni on Aug. 21, 1984 for a Hypodermic Needle Disposal System; U.S. Pat. No. 4,494,652 issued to Nelson et al. on Jan. 22, 1985 for a Container For Sharps; U.S. Pat. No. 4,576,281 issued to Kirksey on Mar. 18, 1986 for a Disposable Syringe Needle Separation and Storage Box; U.S. Pat. No. 4,715,498 issued to Hanifl on Dec. 29, 1987 for a Sharps Disposal System; U.S. Pat. No. 4,667,821 issued to Shillington on May 26, 1987 for a Swivel Top Closure For Phlebotomy Container; and U.S. Pat. No. 4,972,950 issued to Shillington on Nov. 27, 1990 for a Secure Disposable Container Assembly.

Medical waste, including used sharps, clinical specimens, as well as medical and biological devices is typically disposed of by incineration. Large hospitals and medical complexes often have their own incinerators to handle the large volume of medical wastes they produce. Such institutions typically have procedures for the collection of medical waste containers and transportation from their point of origin to the incinerator.

However, small hospitals, clinics and rural medical facilities often do not have waste incineration facilities on site and must rely on waste haulers to dispose of this medical waste. In recent years, state and federal governments have enacted regulations governing the disposal of contaminated medical wastes such as sharps, clinical specimens and medical or biological devices. Such regulations may provide for the disposal of medical waste into the main stream of conventional, non-toxic waste disposal systems, such as landfills only when the waste is properly contained. Further some medical waste generators have been required to ship their waste to authorized incinerators to comply with such regulations.

In addition to the generation of medical wastes from classic sources such as hospitals and clinics, contaminated sharps in need of proper disposal are generated by millions of people who are authorized to give themselves injections of prescribed drugs in their own homes. For example, diabetics often self administer two or more injections of insulin daily, each time using a different needle and syringe. Contaminated medical waste generated in such an environment is generally not properly contained but often finds its way into the local landfills, contrary to state and federal regulation.

While the medical waste containers of the prior art and specifically those cited above all solve other problems of the prior art and are capable of receiving used sharps, none are leak proof and puncture proof such that they may be safely and routinely transported, shipped by a common carrier, or sent through the mail from their point of origin to an incinerator or landfill. Further, none are specifically adapted to be employed by non-medical personnel, such as diabetics, in non-medical environments. Thus, there is a need for a container for disposing of medical wastes such as sharps, clinical specimens and medical or biological devices and etiological agents which is leak and puncture proof and which may be routinely shipped through the mail or other carrier, which can be routinely employed by non-medical personnel or the general public, without the need for otherwise special precautions and which is adapted to be incinerated or otherwise disposed of along with its contents.

SUMMARY OF THE INVENTION AND ADVANTAGES

The subject invention is directed toward a container for disposing of hazardous, wastes and includes an inner receptacle which is adapted to receive and contain the contaminated wastes and an impact resistent outer container. The inner receptacle is disposed within the outer container. The container also includes a fluid barrier which is located between the inner receptacle and the outer container. The fluid barrier acts as an intermediate containment system which prevents any fluid from passing from the inner receptacle to the outer container in the unlikely event that the inner receptacle is ruptured. The inner receptacle and the outer container are then disposed within a corrugated cardboard box which may be transported from the point of origin of the medical waste to an incinerator, or landfill via a common carrier or even the mail. The box may be preaddressed and can be coded for monitoring or tracking by the dispensing agent, mail or common carrier and the incinerator or landfill. The container is leak and puncture proof, impact resistent and stackable one on top of the other for ease of storage, shipping and incineration. In this way, the subject invention overcomes the problems in the prior art in a container for disposing of hazardous medical waste such as sharps, clinical specimens, medical and biological devices or etiological agents which may be conveniently employed in hospitals, labs, testing facilities, industries, by clinics, veterinarians and even by non-medical professionals, such as diabetics, who self administer insulin on a regular basis to properly dispose of sharps and other medical waste in a leak and puncture proof container which is specifically designed for shipping via common carrier or mail.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

The subject invention is directed toward an efficient, convenient, leak proof, puncture proof container for disposing of contaminated toxic medical waste, (medical waste) including needles, syringes, scalpels, etc. (hereinafter "sharps") as well as clinical specimens, medical and biological devices or etiological agents. The container is specifically adapted to accept and store contaminated medical waste and to ship this waste through either a common carrier or the mail from its point of origin to an incinerator or landfill located at a location remote from the point of origin.

Figure 2:
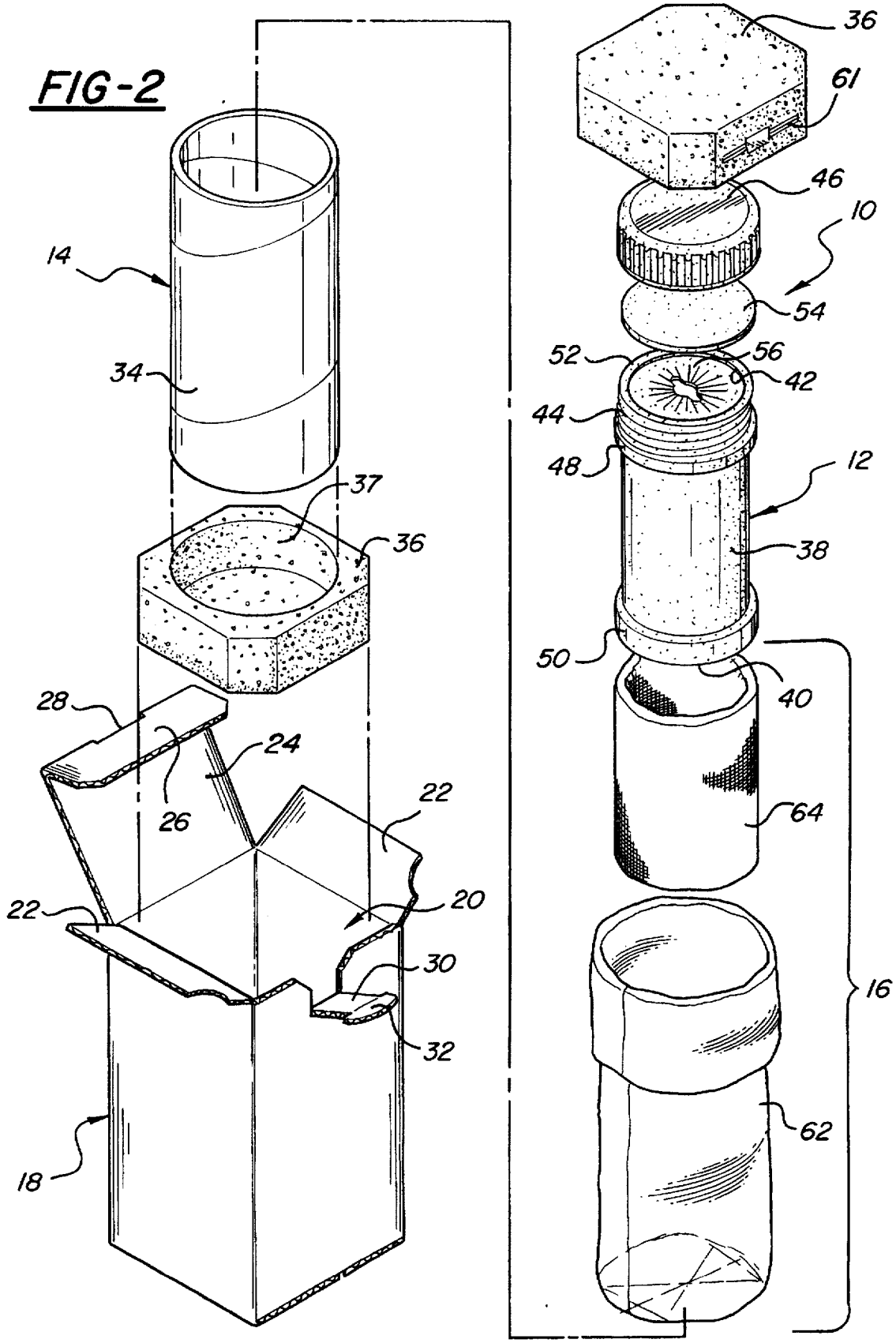
FIG. 2 is an exploded assembly view of the various components of the container of the subject invention.

The assembly which makes up the container of the subject invention is shown generally at 10 in the exploded view of FIG. 2. The container 10 includes an inner receptacle, generally indicated at 12, and an impact resistent outer container 14. The inner receptacle 12 is specifically adapted to receive and contain medical waste and is disposed within the outer container 14. For example and by way of explanation and not by limitation, the inner receptacle 12 is shown with a used scalpel 13, syringe with needle 15 and a used I.V. tube with needle 17 enclosed therein. A small amount of fluid 19 is also shown. The container 10 also includes a fluid barrier, generally indicated as 16 in FIG. 2. This fluid barrier 16 is located between the inner receptacle 12 and the outer container 14. The fluid barrier 16 acts as an intermediate containment system and prevents any fluid from passing from the inner receptacle 12 to the outer container 14 in the unlikely event that the inner receptacle is ruptured as will be discussed in further detail below.

The whole assembly of the inner receptacle 12, the outer container 14 as well as the fluid barrier 16 is ultimately disposed within a corrugated cardboard box, generally indicated at 18. The box 18 may be of any configuration, but in the best mode contemplated by the inventors, is a six sided rectangular shaped cardboard box having a closable open end, generally shown at 20. The open end 20 includes a pair of opposed flaps 22 which are foldable over the opening and a lid 24 with a creased lip 26 extendable in a direction transverse to the lid 24. The lid 24 also includes a slot 28 extending approximately along the line of the crease defining the lip 26. When the flaps 22 are folded toward one another and the lid 24 is folded over the flaps 22, a tongue 30 having an enlarge head 32 is receivable in the slot 28 in such a way as to lock the lid 24 in this closed position. Due to the enlarged shape of the head 32, the tongue 30 may not be removed from the slot 28 without damaging the slot 28, tongue 30 or both. Any such damage to the box 18 indicates unauthorized tampering of a closed, sealed box 18 of the container 10.

Figure 1:
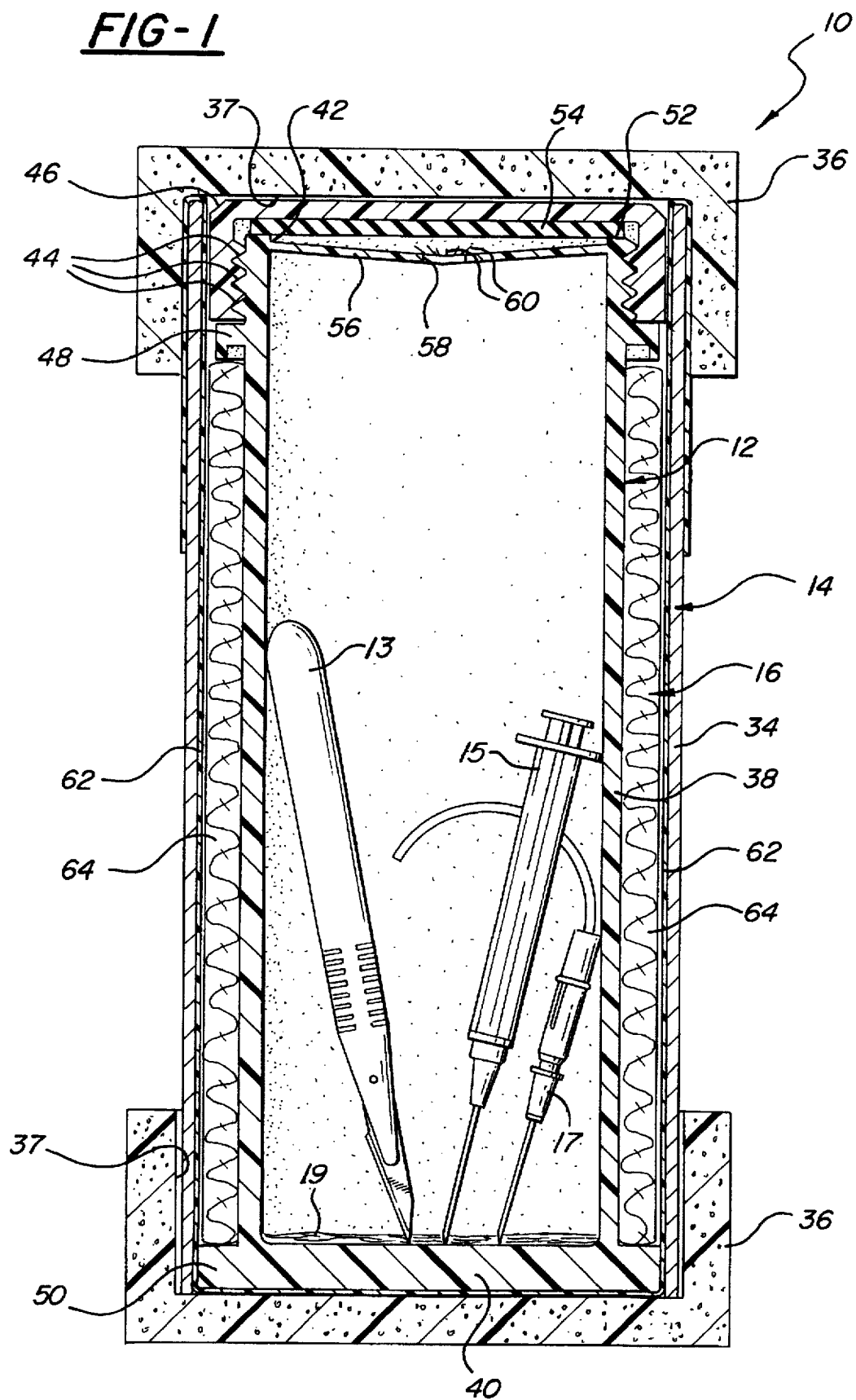
FIG. 1 is a cross-sectional side view of the inner receptacle, outer container and the fluid barrier of the container of the subject invention.

Referring now to both FIGS. 1 and 2, the impact resistent outer container 14 is an open ended cylindrical tube 34 made of sturdy, shock resistent kraft paper. The outer container 14 also includes a pair of polyethylene foam bead end caps 36. The end caps 36 have cylindrically shaped sockets 37 which accept the open ends of the cylindrical tube 34 and are thus removably disposed on either end of the cylinder 34. The outer impact container thus completely encloses the inner receptacle 12 and the fluid barrier 16 and protects the contents from rupture due to shock or any other type of impact.

The inner receptacle 12 includes a high density polyethylene grade 7040D plastic cylindrical body 38 having a closed end or bottom 40 and an open end 42 disposed opposite the closed end. The cylindrical body 38 also includes male threads 44 disposed on a portion of its circumference adjacent its open end 42. A threadably removable high density polyethylene grade 7R156 cap 46 is adapted to be screwed onto the open end 42 of the body 38 and thereby close the open end 42 such that the inner receptacle 12 is sealed shut when the cap 46 is so disposed.

The body 38 also includes a pair of plastic flanges 48, 50. Flange 48 is molded to body 38. The flange 50 is sonically welded to the body. Both flanges are disposed about the cylindrical periphery thereof for strengthening the body of the receptacle 12. The flanges 48, 50 are spaced relative to one another with the flange 48 located adjacent to the last male thread 44 on the open end 42 of the cap 46 and the flange 50 located near the bottom 40 of the body 38 of the inner receptacle 12.

Figure 3:
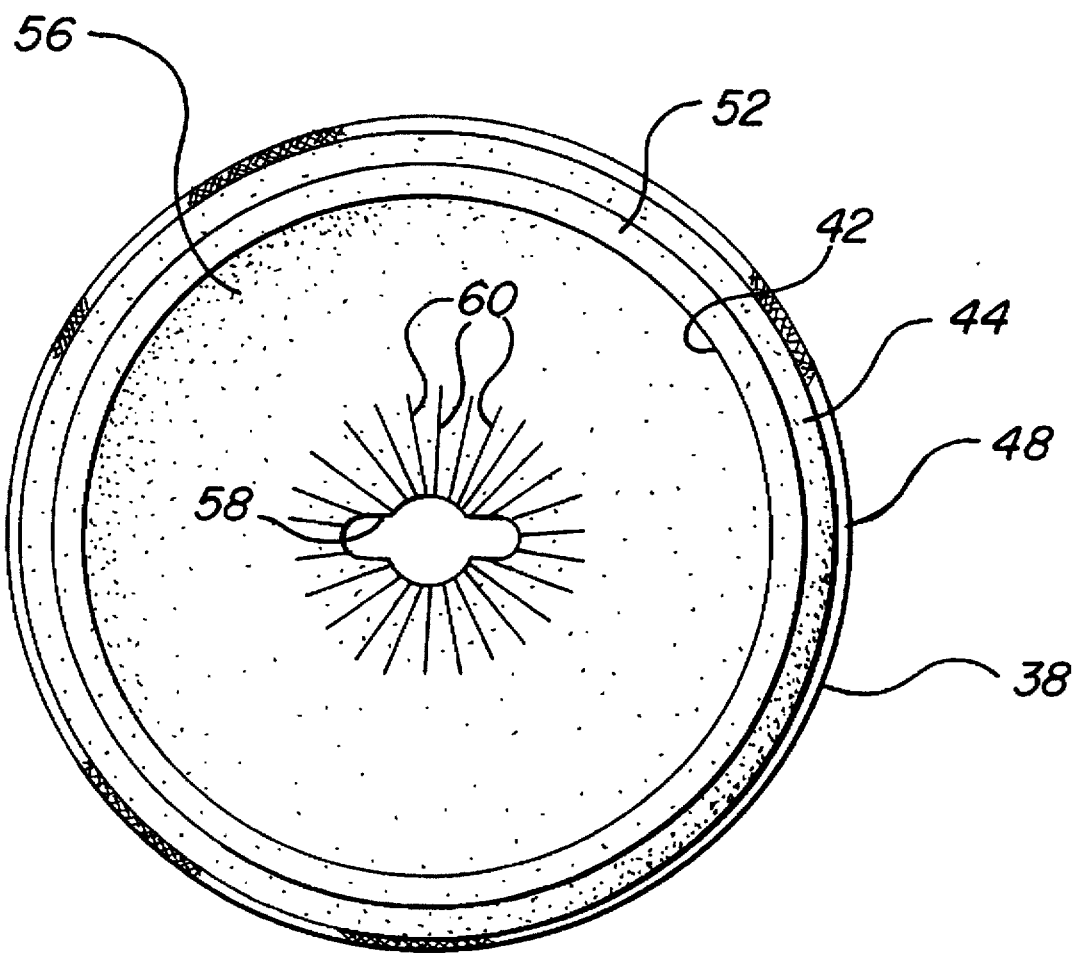
FIG. 3 is a top view of the open end of the inner receptacle having a sealing member disposed across the opening.

The body 38 also defines an upper rim 52. A circular, neoprene gasket 54 is disposed between the rim 52 and the threaded cap 46 to form a seal therebetween and thus prevents any leakage from the inner receptacle 12 at the capped end of the body 38. The gasket 54 is made of a commercial neoprene [40 duro style NO10] ASTM D-2000- Type BC. In addition to the gasket 54, and as best shown in FIGS. 2 and 3, a conically shaped sealing member 56 is disposed within the opening 42 of the body 38 of the inner receptacle. The sealing member 56 has an aperture 58 which allows medical waste such as used sharps, to enter the inner receptacle 12 but otherwise denies access to the interior of the receptacle. The sealing member 56 is made of low density polyethylene Grade F-18D012. The aperture 58 and the sealing member 56 includes a keyhole shaped opening which is centrally located on the sealing member 56. A plurality of slots 60 extend radially outward from the keyhole 58 which allows the sealing member 56 to flex and except waste of varying sizes. In this way, while the inner receptacle 12 receives such wastes, the sealing member prevents used sharps from easily being removed from the receptacle 12 once they have been deposited there.

As indicated earlier, in addition to the sealable inner receptacle 12 and the impact resistent outer container 14, the subject invention also includes a fluid barrier 16 which is disposed between the inner receptacle 12 and the outer container 14 which further insures that no fluid passes from the inner receptacle to the outer container. This is accomplished as follows:

The fluid barrier 16 includes a polyethylene liner 62 having an open end. The inner receptacle 12 is adapted to be disposed within the liner 62 with the liner 62 being sealable at its open end using, for example, a conventional twist tie 61 shown taped to the end cap 36 in FIG. 2. However, it will be appreciated that any other means may be used to seal the liner 62. In addition to the liner 62, the fluid barrier 16 also includes an open ended cylindrically shaped absorbent shield 64 which is disposed about the circumference of the body 38 of the inner receptacle 12 and between the pair of flanges 48, 50. The shield 64 if made of cotton or wooden fiber and coated with a durable absorbent facing which will absorb any fluid in the unlikely event that some is present between the inner receptacle 12 and the liner 62.

As such, the fluid barrier 16, through the liner 62 and the absorbent shield 64, prevents any fluid from passing from the inner receptacle 12 to the outer container 14. Because the inner receptacle 12 and the fluid barrier 16 are disposed within the outer container 14, the assembly is leak proof, puncture proof, and impact resistent. Further, and when this subassembly is disposed within the cardboard box, the container may be stacked one on top of the other to store, ship or incinerate used sharps in a manner which ensures the integrity of the containment of the hazardous wastes.

The invention has been described in an illustrative manner, and it is to be understood that the terminology which has been used is intended to be in the nature of words of description rather than of limitation. Obviously, many modifications and variations of the present invention in light of the above teachings may be made. It is, therefore, to be understood that the invention may be practiced otherwise than as specifically described.

What is claimed is:

1. A container for disposing of hazardous waste, said container comprising:

an inner receptacle adapted to receive and contain hazardous waste, said inner receptacle including a body having a closed end and an open end disposed opposite said closed end, said open end of said body defining an upper rim, said body further including threads disposed about a portion of its circumference at its open end and a threadably removable cap adapted to sealingly close said open end of said body, a gasket disposed between said rim and said threaded cap to form a seal therebetween and prevent leakage from said inner receptacle;

an impact resistant outer container, said inner receptacle being disposed within said outer container, said outer container including a sleeve with at least one open end and having at least one removable end cap which defines a socket and which is disposed over said open end of said sleeve to completely enclose said inner receptacle; and a fluid barrier disposed between said inner receptacle and said outer container, said fluid barrier including a polyethylene liner having an open end, said inner receptacle adapted to be disposed within said liner with said liner being sealable at its open end, said fluid barrier further including an absorbent shield disposed about at least a portion of said inner receptacle and between said liner and said inner receptacle for absorbing any liquid present between said inner container and said liner, said fluid barrier preventing any fluid from passing from said inner receptacle to said outer container.

2. A container as set forth in claim 1 further characterized by said inner receptacle and outer container disposed within a cardboard box which may be transported from one point to another through the mail.

3. A container as set forth in claim 1 further characterized by said impact resistent outer container including an open ended cylinder with a pair of end caps removably disposed on either end of said cylinder to completely enclose said inner receptacle and said fluid barrier.

4. A container as set forth in claim 3 further characterized by said open ended cylinder being made of kraft paper, said end caps being made of polyethylene foam bead.

5. A container as set forth in claim 4 further characterized by said body being cylindrical and including a pair of flanges disposed about the cylindrical periphery thereof and spaced relative to one another for strengthening said body of said receptacle.

6. A container as set forth in claim 5 further characterized by said absorbent shield being cylindrical in shape and disposed about the circumference of said body of said inner receptacle between said pair of flanges, said shield being made of cotton type fiber and coated with a durable facing.

7. A container as set forth in claim 6 further characterized by including a conically shaped sealing member disposed within the opening of said body of said inner receptacle and including an aperture which allows medical waste to enter said inner receptacle but otherwise limits access to the interior of said inner receptacle.

8. A container as set forth in claim 7 further characterized by said sealing member being made of low density polyethylene, said aperture in said sealing member including a shaped opening centrally located on said sealing member and a plurality of slots extending radially outward from said keyhole which allows said sealing member to flex and accept waste of varying sizes.

* * * * *